US012731692B1

(12) United States Patent
Banerjee et al.

(10) Patent No.: US 12,731,692 B1
(45) Date of Patent: Sep. 8, 2026

(54) PREDICTING THE OUTCOME OF A CLINICAL TRIAL USING A MACHINE LEARNING MODEL

(71) Applicant: NEUMORA THERAPEUTICS, INC., Watertown, MA (US)

(72) Inventors: Tathagata Banerjee, Waltham, MA (US); Karin Comer Knudson, Somerville, MA (US)

(73) Assignee: Neumora Therapeutics, Inc., Watertown, MA (US)

( * ) Notice: Subject to any disclaimer, the term of this patent is extended or adjusted under 35 U.S.C. 154(b) by 0 days.

(21) Appl. No.: 19/057,860

(22) Filed: Feb. 19, 2025

Related U.S. Application Data

(60) Provisional application No. 63/571,360, filed on Mar. 28, 2024.

(51) Int. Cl.
*G16H 50/20* (2018.01)
*G16H 10/60* (2018.01)

(52) U.S. Cl.
CPC ............ *G16H 50/20* (2018.01); *G16H 10/60* (2018.01)

(58) Field of Classification Search
CPC .............................. G16H 50/20; G16H 10/60
See application file for complete search history.

(56) References Cited

U.S. PATENT DOCUMENTS 11,789,837 B1 * 10/2023 Jain .................... G06F 11/3006 709/224
2020/0105380 A1 * 4/2020 Ennist .................. G16H 50/70
2020/0234800 A1 * 7/2020 Will ...................... G16H 10/20
2021/0142910 A1 * 5/2021 Hafez .................... G16H 20/40
2025/0111907 A1 4/2025 Rudrapatna et al.

FOREIGN PATENT DOCUMENTS

WO WO 2025/072661 A1 4/2025

OTHER PUBLICATIONS

Pearson R, Pisner D, Meyer B, Shumake J, Beevers CG. A machine learning ensemble to predict treatment outcomes following an Internet intervention for depression. Psychological Medicine. 2019; (Year: 2019).*

Murray et al., "A Bayesian machine learning approach for optimizing dynamic treatment regimes," Journal of the American Statistical Association, 2018, 113(523):1255-1267, 28 pages (Author Manuscript).

Wu et al., "Bayesian Machine Learning: EEGVMEG signal processing measurements," IEEE Signal Processing Magazine, Dec. 29, 2015, 33(1):14-36.

* cited by examiner

*Primary Examiner* — Matthew L Hamilton
(74) *Attorney, Agent, or Firm* — Fish & Richardson P.C.

(57) ABSTRACT

Methods, systems, and apparatus, including computer programs encoded on a computer storage medium, for performing a simulation to predict an outcome of a clinical trial having a set of inclusion criteria. According to one aspect, a method comprises: obtaining data defining a simulated population of subjects satisfying the inclusion criteria for the clinical trial, wherein each subject in the simulated population of subjects is associated with a feature set characterizing the subject; generating, for each subject in the simulated population of subjects, a plurality of predicted response scores for the subject using an ensemble of machine learning models; and determining the predicted outcome of the clinical trial based on the plurality of response scores.

20 Claims, 11 Drawing Sheets

PREDICTING THE OUTCOME OF A CLINICAL TRIAL USING A MACHINE LEARNING MODEL

CROSS-REFERENCE TO RELATED APPLICATIONS

This application claims priority to U.S. Provisional Application No. 63/571,360, filed on Mar. 28, 2024. The disclosure of the prior application is considered part of and is incorporated by reference in the disclosure of this application.

BACKGROUND

This specification relates to processing data using machine learning models.

Machine learning models receive an input and generate an output, e.g., a predicted output, based on the received input. Some machine learning models are parametric models and generate the output based on the received input and on values of the parameters of the model.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

A clinical trial is a type of research study that is designed to investigate the effects of a treatment on human participants. In a clinical trial, participants can be assigned to one or more groups (which can include a control group) to evaluate the effects of the treatment on biomedical or behavioral outcomes. Participants in a clinical trial can be selected based on various types of criteria.

SUMMARY

This specification describes a system implemented as computer programs on one or more computers in one or more locations for predicting an outcome of a clinical trial that has a set of inclusion criteria.

A clinical trial is a type of research study on human participants that is designed to answer research questions about drugs, vaccines, and other treatments.

A treatment group is a group of subjects in a clinical trial that receives a treatment that is being studied e.g., a drug or vaccine.

A control group is a group of participants in a clinical trial that does not receive a treatment that is being studied.

A control group can be compared to a treatment group to measure the effectiveness of the treatment.

According to a first aspect, there is provided a method performed by one or more computers, the method comprising: performing a simulation to predict an outcome of a clinical trial having a set of inclusion criteria, comprising: obtaining data defining a simulated population of subjects satisfying the inclusion criteria for the clinical trial, wherein each subject in the simulated population of subjects is associated with a feature set characterizing the subject; generating, for each subject in the simulated population of subjects, a plurality of predicted response scores for the subject, wherein each predicted response score characterizes a predicted change in a medical condition of the subject during the clinical trial, wherein for each subject, generating the plurality of predicted response scores for the subject comprises: processing, by each machine learning model in an ensemble of machine learning models, the feature set characterizing the subject in accordance with values of a set of model parameters of the machine learning model to generate a respective predicted response score for the subject; and determining the predicted outcome of the clinical trial based on the plurality of response scores for each subject in the simulated population of subjects.

In some implementations, each machine learning model in the ensemble of machine learning models has: (i) a same model architecture, and (ii) a respective set of model parameters having values that are specific to the machine learning model.

In some implementations, the ensemble of machine learning models is generated by operations comprising: training a probabilistic machine learning model to process an input feature set characterizing a subject to generate a predicted response score for the subject, wherein each model parameter in a set of model parameters of the probabilistic machine learning model is associated with a respective distribution over possible values of the model parameter; and generating the ensemble of machine learning models using the probabilistic machine learning model.

In some implementations, each machine learning model in the ensemble of machine learning models has a same model architecture as the probabilistic machine learning model; and generating the ensemble of machine learning models using the probabilistic machine learning model comprises, for each machine learning model in the ensemble of machine learning models: generating the machine learning model as an instance of the probabilistic machine learning model by, for each model parameter of the probabilistic machine learning model, sampling a respective single value for the model parameter from the distribution over possible values of the model parameter.

In some implementations, the probabilistic machine learning model comprises one or more of: a neural network model; or a linear regression model; or a decision tree model.

In some implementations, obtaining data defining the simulated population of subjects satisfying the inclusion criteria for the clinical trial comprises: generating a distribution over a space of feature sets based on the set of inclusion criteria for the clinical trial; and generating the respective feature set for each subject in the simulated population of subjects by sampling from the distribution over the space of feature sets.

In some implementations, generating the distribution over the space of feature sets based on the set of inclusion criteria for the clinical trial comprises: identifying a real-world population of subjects that satisfy the set of inclusion criteria; obtaining a collection of feature sets that includes a respective feature set for each subject in the real-world population of subjects that satisfy the inclusion criteria; and generating the distribution over the space of feature sets by fitting the distribution over the space of feature sets to the collection of feature sets for the real-world population of subjects that satisfy the inclusion criteria.

In some implementations, the clinical trial is a clinical trial for a drug; and the simulated population of subjects is a treatment group that receive the drug; and each predicted response score characterizes a predicted change in the medical condition of the subject during the clinical trial as a result of receiving the drug.

In some implementations, determining the predicted outcome of the clinical trial for the drug based on the plurality of response scores for each subject in the simulated population of subjects comprises: determining a measure of central tendency of the response scores for the subjects in the simulated population of subjects; and determining a measure of dispersion of the response scores for the subjects in the simulated population of subjects.

In some implementations, the drug is a drug for treating depression; and each predicted response score for each subject characterizes a predicted change in a measure of depression of the subject during the clinical trial.

In some implementations, the drug is a drug for treating a neurodegenerative disease; and each predicted response score for each subject characterizes a predicted change in a measure of severity of the neurodegenerative disease.

In some implementations, the neurodegenerative disease is Alzheimer's disease, or Parkinson's disease, or Huntington's disease, or multiple sclerosis.

In some implementations, performing the simulation to predict the outcome of the clinical trial having the set of inclusion criteria further comprises: obtaining data defining a second simulated population of subjects satisfying the inclusion criteria for the clinical trial, wherein the second simulated population of subjects is a control group that does not receive the drug; and generating, for each subject in the second simulated population of subjects, a plurality of predicted response scores for the subject;

In some implementations, the predicted outcome of the clinical trial for the drug is based on both: (i) the plurality of response scores for each subject in the simulated population of subjects that is the treatment group, and (ii) the plurality of response scores for each subject in the second simulated population of subjects that is the control group.

In some implementations, the predicted outcome of the clinical trial is based on a measure of difference between: (i) the plurality of response scores for each subject in the simulated population of subjects that is the treatment group, and (ii) the plurality of response scores for each subject in the second simulated population of subjects that is the control group.

In some implementations, the method further comprises selecting the set of inclusion criteria for the clinical trial based at least in part on the predicted outcome of the clinical trial having the inclusion criteria.

In some implementations, the clinical trial is for a drug, and the method further comprises, for each of one or more real-world subjects: determining that the real-world subject satisfies the set of inclusion criteria for the clinical trial; and in response, determining that the real-world subject should receive the drug as part of the clinical trial.

In some implementations, the method further comprises, for each of the one or more real-world subjects administering the drug to the real-world subject in response to determining that the real-world subject should receive the drug as part of the clinical trial.

In some implementations, for each subject in the simulated population of subjects, the feature set characterizing the subject comprises subject-specific features characterizing one or more: demographic features of the subject; age of the subject; medical diagnoses of the subject; physiological features of the subject derived from analysis of tissue, blood, or urine samples from the subject; or a severity of a medical condition of the subject.

In some implementations, for each subject in the simulated population of subjects, the feature set characterizing the subject comprises site-level features characterizing a site at which the subject undergoes the clinical trial; where the site-level features characterize one or more of: a geographic location of the site, a facility type at the site, an experience level of investigators at a site, or a capacity of the site.

In some implementations, for each subject in the simulated population of subjects, the feature set characterizing the subject comprises trial-level features characterizing one or more of: a duration of the clinical trial; a number of sites included in the clinical trial; a number of arms in the clinical trial; a relative size of a control group in the clinical trial; or a number of subjects included in the clinical trial.

In some implementations, the method further comprises performing an automated search through a space of possible inclusion criteria to optimize a predicted outcome of the clinical trial.

In some implementations, performing the automated search through the space of possible inclusion criteria to optimize the predicted outcome of the clinical trial comprises: identifying a plurality of possible sets of inclusion criteria for the clinical trial; performing, for each set of inclusion criteria in the plurality of possible sets of inclusion criteria, a respective simulation to predict an outcome of a clinical trial having the set of inclusion criteria; and selecting a final set of inclusion criteria based at least in part on the predicted outcomes for the plurality of possible sets of inclusion criteria.

In some implementations, the automated search through the space of possible inclusion criteria is performed in accordance with a black box optimization technique.

In some implementations, the automated search through the space of possible inclusion criteria is subject to one or more constraints; wherein the one or more constraints include a constraint that, for a set of inclusion criteria to be feasible, at least a number or percentage of real-world subjects are predicted to satisfy the inclusion criteria.

According to another aspect, there is provided a system comprising: one or more computers; and one or more storage devices communicatively coupled to the one or more computers, wherein the one or more storage devices store instructions that, when executed by the one or more computers, cause the one or more computers to perform operations of the methods described herein.

According to another aspect, there are provided one or more non-transitory computer storage media storing instructions that when executed by one or more computers cause the one or more computers to perform operations of the methods described herein.

According to another aspect, there is provided a method comprising: determining one or more predicted outcomes of a clinical trial, e.g., by the computational processes described throughout this document, wherein the clinical trial is for a drug; determining a set of inclusion criteria for the clinical trial based on the predicted outcome; determining that a real-world subject (patient) satisfies the inclusion criteria for the clinical trial; and, in response, determining that the real-world subject should receive the drug, and optionally, administering the drug to the real-world subject.

Particular embodiments of the subject matter described in this specification can be implemented so as to realize one or more of the following advantages.

A clinical trial simulation system can use a single machine learning model to predict a point estimate of a measure of success of a clinical trial. However, generating a point estimate does not account for uncertainty in the parameters of the model and can limit the accuracy of simulations of clinical trials. The simulation system described in this specification uses an ensemble of models to generate a distribution of trial outcomes rather than one model that generates a point estimate of a trial outcome. This allows the simulation system to use uncertainty estimates to simulate a new group of participants more accurately and comprehensively than conventional methods. In a follow up real-world clinical trial to the simulation, the chosen participants for a trial can be enriched to optimize better treatment of patients based on the result of the simulation.

The simulation system can perform an automated constrained optimization over the inclusion parameters of the trial to optimize the predicted outcome of the clinical trial. The automated constrained optimization can identify inclusion parameters for clinical trials that are likely to succeed to better design a real-world clinical trial. The simulation system can also be used to identify clinical trials that are unlikely to succeed, and thereby reduce wastage of resources on failed clinical trials.

The clinical trial simulation system described in this specification utilizes a set of machine learning models to understand how treatment group responses, control group responses, and the relationship between them changes as characteristics of the participants, sites, and trial change. The simulation system can process a hierarchical feature set and has the flexibility to combine individual level features (e.g., age and sex of participants) with site level features (e.g., site location) and trial level features (e.g., size of study) when making predictions. The simulation system can process the features using the ensemble of models to generate probability distributions for treatment group responses, control group responses, and the relationship between them as opposed to a conventional model that generates point estimates only.

Furthermore, the simulation system described in this specification reduces the consumption of computational resources (e.g., memory and computing power) by representing the entire ensemble of machine learning models by the distributional parameters of a single probabilistic model. The simulation system does not need to separately train and store the entire ensemble of different models, and can instead train one probabilistic model with distributions over the values of its weights.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
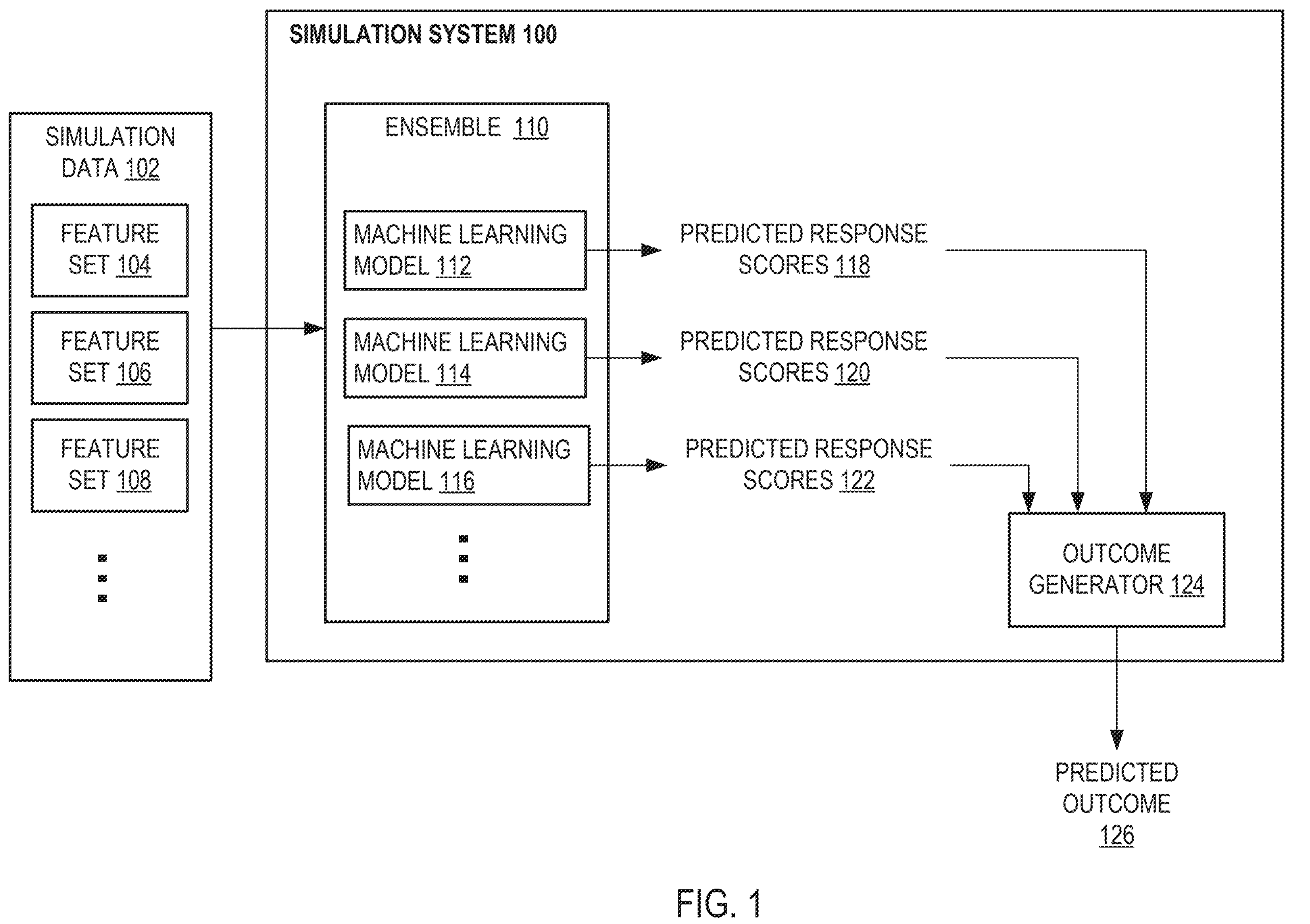
FIG. 1 is a block diagram of an example simulation system.

FIG. 1 shows an example simulation system 100. The simulation system 100 is an example of a system implemented as computer programs on one or more computers in one or more locations in which the systems, components, and techniques described below are implemented.

The simulation system 100 includes an ensemble 110 of machine learning models 112, 114, and 116 and an outcome generator 124. The simulation system can predict an outcome of a clinical trial that has a set of inclusion criteria.

The simulation system 100 processes simulation data 102 that defines a simulated population of subjects that satisfy the inclusion criteria for the clinical trial.

The clinical trial can, for example, be a clinical trial for a drug. The drug can, for example, be a drug for treating a mental illness (e.g., depression, anxiety, etc.), a drug for treating a neurogenerative disease (e.g., Alzheimer's disease, Parkinson's disease, Huntington's disease, multiple sclerosis etc.), or a drug for treating a physical disease (e.g., epilepsy, migraines, heart disease etc.). The simulated population of subjects can be a treatment group that receives the drug or a control group that does not receive the drug.

The inclusion criteria can define features of the target population that are relevant to the research question of the clinical trial. The inclusion criteria can, for example, include type and stage of disease (e.g., early, late, etc.), previous treatment history (e.g., none, types of drugs used for treatment in the past, etc.), age range (e.g., 15-40, 70-80, 50-100, etc.), gender, etc. The inclusion criteria can be specified, for example, by a user. As another example, the inclusion criteria can be specified by an up-stream system e.g., an optimization system. Selecting a set of inclusion criteria using an optimization system is described further below with reference to FIG. 5.

The simulation data 102 includes a respective feature set 104, 106, and 108 characterizing each subject in the simulated population. The simulated population can include any appropriate number of simulated subjects e.g., 100, 1000, 10,000, or 100,000 subjects. The number of subjects in the simulated population can be specified e.g., by a user. The simulation system 100 can obtain data defining the simulated population of subjects satisfying the inclusion criteria for the clinical trial by generating the respective feature set for each subject in the simulated population of subjects by sampling features from the distribution over the space of feature sets.

The simulation data 102 can be, for example, tabular data describing a population of real-world subjects, each of which is associated with a respective set of real-world features. The set of real-world features can include personal characteristics associated with the respective real-world subject.

The system 100 can first generate a distribution over a space of feature sets based on the set of inclusion criteria for the clinical trial. In order to generate the distribution, the simulation system 100 can identify a real-world population of subjects that satisfy the set of inclusion criteria. The system 100 can obtain a collection of feature sets that includes a respective feature set for each subject in the real-world population of subjects that satisfy the inclusion criteria. For example, if the inclusion criteria includes an age range of 15-40 and a disease stage of late, the collection of feature sets can include the respective feature sets for all subjects in the real world population between the ages of 15 and 40 who have a late stage of the disease.

The system 100 can generate the distribution over the space of feature sets by fitting the distribution over the space of feature sets to the collection of feature sets for the real-world population of subjects that satisfy the inclusion criteria. The simulation system 100 can extract the subset of real-world subjects that satisfy the set of inclusion criteria. In some examples, the simulation system can then sample with replacement from the feature sets associated with these subjects. In other examples, the simulation system can fit a distribution function (e.g., a mixture of Gaussians) to the feature sets of these real-world subjects. The simulation system can then sample from that distribution in order to obtain the feature sets 104, 106, and 108 for the simulated subjects. The simulation system can use any appropriate method of fitting a distribution function to a set of data by estimating the parameters of the distribution function e.g., maximum likelihood estimation, method of moments, Bayesian methods, least squares, etc.

The simulation system 100 can then generate the respective feature set 104, 106, and 108 for each subject in the simulated population of subjects by sampling from the distribution over the space of feature sets.

Each feature set 104, 106, and 108 is a feature representation characterizing a different subject. Each feature set 104, 106, and 108, is a collection of features that represent data characterizing the respective subject. The features in each feature set can include one or more of: subject specific features, site level features, or trial level features. The subject specific features can include, for example, one or more demographic features of the subject (e.g., age of the subject, medical diagnoses of the subject), physiological features of the subject (e.g., features derived from analysis of tissue, blood, or urine samples from the subject), or a severity of a medical condition of the subject (e.g. severity on an appetite-related item within a questionnaire for depression severity, rating of the severity of grandiosity within a larger standard clinical scale for schizophrenia, a severity of depression, a severity of Alzheimer's, etc.). The site-level features can include, for example, features characterizing a site at which the subject undergoes the clinical trial (e.g., a geographic location of the site or a facility type at the site), measures of experience level of investigators at a site (e.g. a number of previous clinical trials in the same disease area), measures of the size/capacity of a site (in terms of number of subjects enrolled). The trial level features can include, for example, a duration of the clinical trial (e.g., 60 days, 130 days, 200 days, etc.), a number of sites included in the clinical trial (e.g., 1 site, 3 sites, 10 sites, etc.), a number of subjects included in the clinical trial (e.g., 20 subjects, 100, subjects, 1000 subjects, etc.), the number of arms of the trial (e.g., 2 arms, 3 arms, etc.), or the relative size of the placebo (control group) arm (e.g., one third, one half, etc.).

The ensemble 110 includes multiple machine learning models 112, 114, and 116. The ensemble can include any appropriate number of machine learning models e.g., 10, 100, 1000, 10,000, etc. Each of the machine learning models 112, 114, and 116 can be any appropriate model that can be configured to process a feature set characterizing a subject to generate a predicted response score for the subject, e.g., a neural network model, a linear regression model, or a decision tree model.

For each subject in the simulated population, each machine learning model 112, 114, and 116 in the ensemble 110 processes the respective feature set 112, 114, and 116 in accordance with values of a set of model parameters of the machine learning model to generate a respective predicted response score 118, 120, and 122 for the subject.

Each of the machine learning models 112, 114, and 116 can have a same model architecture and a respective set of model parameters that are specific to the machine learning model. The ensemble 110 of machine learning models 112, 114, and 116 can be instances of an underlying probabilistic machine learning model.

Generating the ensemble 110 is described further below with reference to FIG. 3.

The predicted response scores 118, 120, and 122 characterizes a predicted change in a medical condition of the subject during the clinical trial. For example, when the clinical trial is a clinical trial for a drug, the simulated population of subjects can be a treatment group that receives the drug. Each predicted response score can characterize a predicted change in the medical condition of the subject during the clinical trial as a result of receiving the drug. For example, if the drug is a drug for treating depression, each predicted response score 118, 120, and 122 can characterize a predicted change in a measure of depression (e.g., a Beck Depression Inventory (BDI) score, a Hamilton Depression Rating Scale (HDRS) score, etc.) of the subject during the clinical trial. As another example, if the drug is a drug for treating a neurodegenerative disease, each predicted response score 118, 120, and 122 can characterize a predicted change in a measure of severity (e.g., a Clinical Dementia Rating (CDR), a Mini-Mental State Examination (MMSE) score, a Unified Parkinson's Disease Rating Scale (UPDRS) score, a Total Functional Capacity (TFC) score, a Multiple Sclerosis Severity Score (MSSS), etc.) of the neurodegenerative disease. Each predicted response score 118, 120, and 122 can be a number (e.g., 0, 2, 3, etc.).

The outcome generator 124 determines the predicted outcome 126 of the clinical trial based on the response scores 118, 120, and 122 for each subject in the simulated population. The predicted outcome 126 can be a measure of performance of the drug in the clinical trial e.g., an overall effectiveness of the drug. The outcome generator 124 can derive the predicted outcome 126 from the predicted response scores 118, 120, and 122 for the individual subjects. The outcome generator 124 can determine a measure of central tendency of the response scores for the subjects in the simulated population of subjects. The central tendency can be, for example, an average, a median, or a mode of the response scores 118, 120, and 122 generated by the ensemble 110 of machine learning models 112, 144, and 116. The outcome generator 124 can then determine a measure of dispersion of the response scores for the subjects in the simulated population. The measure of dispersion can be, for example, a standard deviation, a variance, etc.

In some examples, the simulation system can predict a treatment group response and a control group response. The simulation system can obtain data that defines a second population of simulated subjects that makes up a control group that will not receive the drug during the clinical trial. When the simulation system predicts both a treatment group response and a control group response, each feature set in the simulation data can include a flag indicating whether each subject is in the treatment group or the control group.

The flag can be, for example, a binary feature identifying each subject as either in the treatment group or the control group. In some examples, the simulation system 100 can generate a predicted response score for each subject in the control group using the ensemble 110 of machine learning models 112, 114, and 116. In other examples, the simulation system 100 can generate a predicted response score for each subject in the control group using a second ensemble of machine learning models. The machine learning models in the second ensemble of machine learning models can be models trained to predict a response score for subjects in a control group.

The predicted outcome 126 can be based on both the response scores 118, 120, and 122 for each subject in the treatment group and the response scores for each subject in the control group. The predicted outcome 126 can be based on a measure of difference between the response scores for each subject in the treatment group and the response for each subject in the control group. The measure of difference can be, for example, a Cohen's D standardized mean difference.

The predicted outcome 126 of the clinical trial generated by the simulation system 100 can be used to enroll real-world subjects in a real-world clinical trial. A real-world clinical trial can be designed to optimize the predicted outcome based on the result of the clinical trial simulated by the simulation system. For example, a real-world clinical trial can be designed to have a treatment group that is likely to respond to a drug. The predicted outcome 126 of the clinical trial generated by the simulation system can indicate whether subjects that satisfy the set of inclusion criteria for the clinical trial are likely to respond to the drug. If subjects that satisfy the set of inclusion criteria in the inclusion criteria in the simulated trial align with a design goal (e.g., having subjects who are likely to respond to the drug) of a real-world clinical trial, real-world subjects for a real-world clinical trial can be selected based on the inclusion criteria for the simulated trial. If a real-world subject satisfies the set of inclusion criteria for the clinical trial, the real-world subject can be selected to receive the drug as a part of the real world clinical trial and the drug can be administered to the real-world subject during the clinical trial.

In some implementations, the simulation system 100 can perform an automated search through a space of possible inclusion criteria to optimize the predicted outcome 126 of the clinical trial. Performing an automated search through a space of possible inclusion criteria is described further below with reference to FIG. 5.

Figure 2:
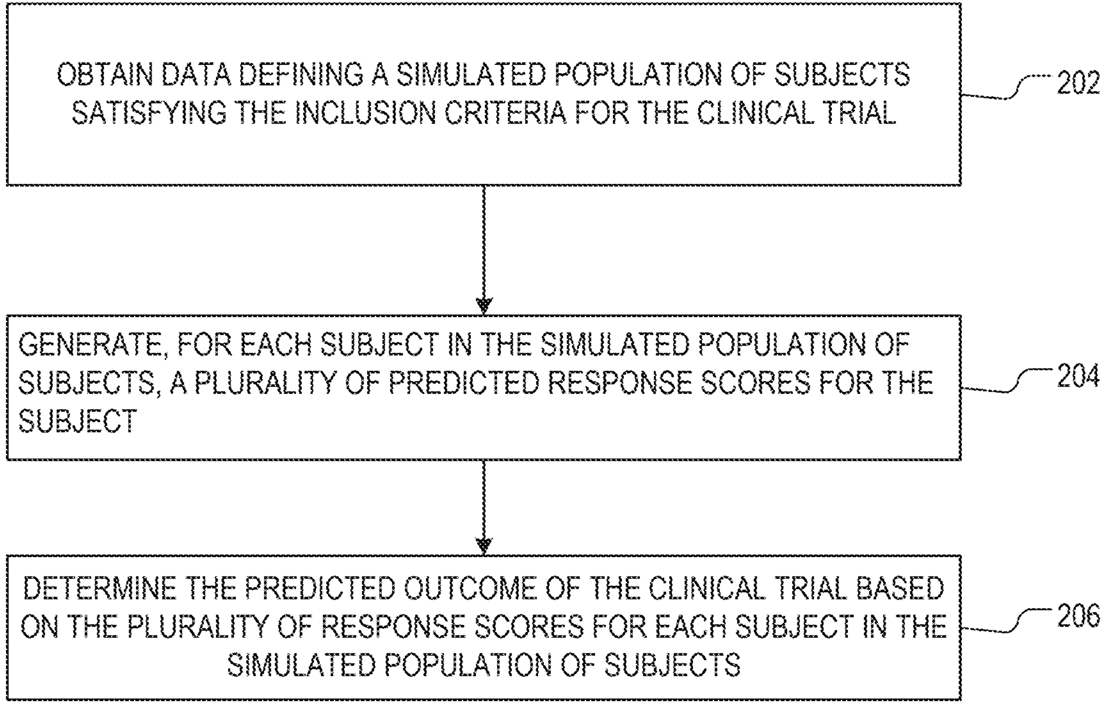
FIG. 2 is a flow diagram of an example process for determining the predicted outcome of a clinical trial.

FIG. 2 is a flow diagram of an example process 200 for determining the predicted outcome of a clinical trial. For convenience, the process 200 will be described as being performed by a system of one or more computers located in one or more locations. For example, a simulation system, e.g., the simulation system 100 of FIG. 1, appropriately programmed in accordance with this specification, can perform the process 200.

The system can obtain data defining a simulated population of subjects satisfying the inclusion criteria for the clinical trial (step 202). Each subject in the simulated population of subjects is associated with a feature set characterizing the subject. Obtaining data defining a simulated population of subjects satisfying the inclusion criteria for a clinical trial is described further below with reference to FIG. 4.

The clinical trial can, for example, be a clinical trial for a drug. The drug can, for example, be a drug for treating a mental illness, a drug for treating a neurogenerative disease, or a drug for treating a physical disease. The simulated population of subjects can be a treatment group that receives the drug or a control group that does not receive the drug.

The inclusion criteria can define features of the target population that are relevant to the research question of the clinical trial. A subject is eligible for inclusion in the clinical trial if the subject satisfies the inclusion criteria. The inclusion criteria can, for example, include type and stage of disease, previous treatment history, age range, gender, etc.

The simulation data includes a respective feature set characterizing each subject in the simulated population. Each feature set can include any appropriate number of features characterizing the subject e.g., 10 features, 100 features, 1000 features, etc.

The system can generate, for each subject in the simulated population of subjects, multiple predicted response scores for each subject in the simulated population of subjects (step 204). Each predicted response score can characterize a predicted change in a medical condition of the subject during the clinical trial. For example, when the clinical trial is a clinical trial for a drug, the simulated population of subjects can be a treatment group that receives the drug. Each predicted response score can characterize a predicted change in the medical condition of the subject during the clinical trial as a result of receiving the drug.

For each subject, the system can generate the multiple predicted response scores for the subject by processing, by each machine learning model in an ensemble of machine learning models, the feature set characterizing the subject in accordance with values of a set of model parameters of the machine learning model to generate a respective predicted response score for the subject.

The ensemble of machine learning models can be instances of an underlying probabilistic machine learning model. Each of the machine learning models can have a same model architecture and a respective set of model parameters that are specific to the machine learning model. Generating an ensemble of machine learning models is described further below with reference to FIG. 3.

The system can determine the predicted outcome of the clinical trial based on the plurality of response scores for each subject in the simulated population of subjects (step 206).

The predicted outcome can be a measure of performance of the drug in the clinical trial e.g., an overall effectiveness of the drug. The system can derive the predicted outcome from the response scores for the individual subjects.

The system can determine a measure of central tendency of the response scores for the subjects in the simulated population of subjects. The central tendency can be, for example, an average, median, or mode of the response scores generated by the ensemble of machine learning models. The system can then determine a measure of dispersion of the response scores for the subjects in the simulated population. The measure of dispersion can be, for example, a standard deviation, a variance, etc.

In some implementations, the system can predict both a treatment group response and a control group response. The system can obtain data defining a second simulated population of subjects satisfying the inclusion criteria for the clinical trial. The second simulated population of subjects can be a control group that does not receive the drug. The system can generate a plurality of predicted response scores for each subject in the second simulated population of subjects using the ensemble of machine learning models. For each subject in the second simulated population, the system can generate multiple predicted response scores for the subject by processing, by each machine learning model in the ensemble of machine learning models, the feature set characterizing the subject in accordance with values of a set of model parameters of the machine learning model to generate a respective predicted response score for the subject.

The predicted outcome of the clinical trial for the drug can be based on both the plurality of response scores for each subject in the simulated population of subjects that is the treatment group, and the plurality of response scores for each subject in the second simulated population of subjects that is the control group. The predicted outcome can be based on a measure of difference between the response scores for each subject in the treatment group and the response scores for each subject in the control group. The measure of difference can be, for example, a Cohen's D standardized mean difference.

Figure 3:
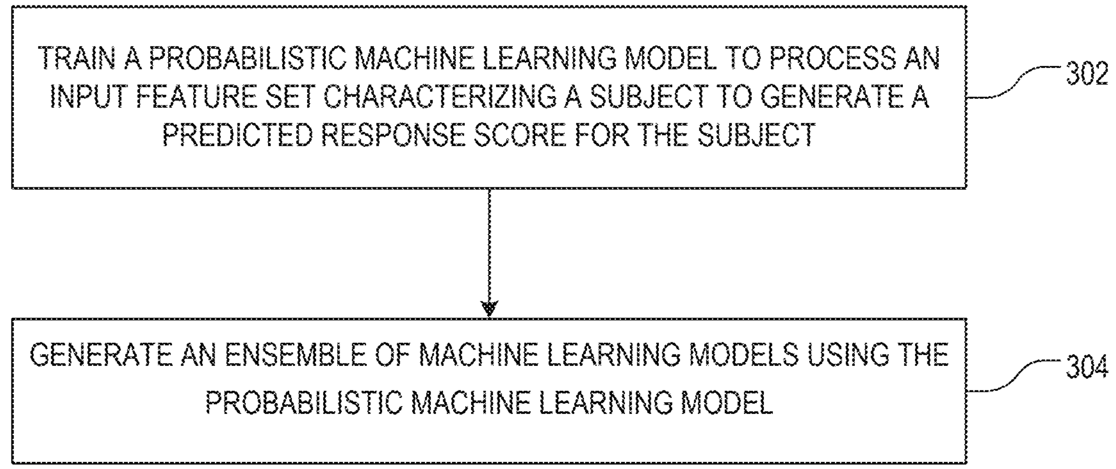
FIG. 3 is a flow diagram of an example process for generating an ensemble of machine learning models.

FIG. 3 is a flow diagram of an example process 300 for generating an ensemble of machine learning models. For convenience, the process 300 will be described as being performed by a system of one or more computers located in one or more locations. For example, a simulation system, e.g., the simulation system 100 of FIG. 1, appropriately programmed in accordance with this specification, can perform the process 300.

The system can train a probabilistic machine learning model to process an input feature set characterizing a subject to generate a predicted response score for the subject (step 302). Each model parameter in a set of model parameters of the probabilistic machine learning model can be associated with a respective distribution over possible values of the model parameter. Each respective distribution can be, for example, a Gaussian distribution parametrized by a mean parameter and a variance parameter.

The probabilistic machine learning model can include one or more of a neural network model, a linear regression model, or a decision tree model. The probabilistic machine learning model can be any appropriate machine learning model that can be configured to process an input feature set and generate a predicted response score. The system can train the probabilistic machine learning model, by a machine learning training technique, using training examples that include a set of features that characterize a subject in a clinical trial and a target response score for the subject that is a ground truth response score. The system can train the probabilistic machine learning model to optimize a loss function that measures a discrepancy between a predicted response score for a subject and the target response score for the subject. Alternatively or in combination, the system can train the probabilistic machine learning model in order to infer the probability distribution of the model parameters given the training data and (optionally) incorporating prior knowledge about the model parameters, e.g., using Markov chain Monte Carlo or variational inference methods.

In some examples, the probabilistic machine learning model can be trained separately for predicting response scores of subjects in a control group. The system can train the probabilistic machine learning model using training examples that include a set of features that characterize a subject in a control group in a clinical trial and a ground truth response score for the subject in the control group. In some examples, the control group can be a control group for a clinical trial for a different drug. The probabilistic model can be trained using the techniques described in Murphy, Kevin P. *Machine learning: a probabilistic perspective*. MIT press, 2012; Murray, Thomas A., Ying Yuan, and Peter F. Thall. "A Bayesian machine learning approach for optimizing dynamic treatment regimes." *Journal of the American Statistical Association* 113.523 (2018): 1255-1267; Wu, Wei, Srikantan Nagarajan, and Zhe Chen. "Bayesian Machine Learning: EEGVMEG signal processing measurements." *IEEE Signal Processing Magazine* 33.1 (2015): 14-36. or any other appropriate training technique.

The system can generate the ensemble of machine learning models using the probabilistic machine learning model (step 304). In some implementations, each machine learning model in the ensemble can have a same architecture as the probabilistic machine learning model. The system can generate each machine learning model as an instance of the probabilistic machine learning model. For each machine learning model in the ensemble of machine learning models, the system can generate the machine learning model as an instance of the probabilistic machine learning model by, for each model parameter of the probabilistic machine learning model, sampling a respective single value for the model parameter from the distribution over possible values of the model parameter.

Figure 4:
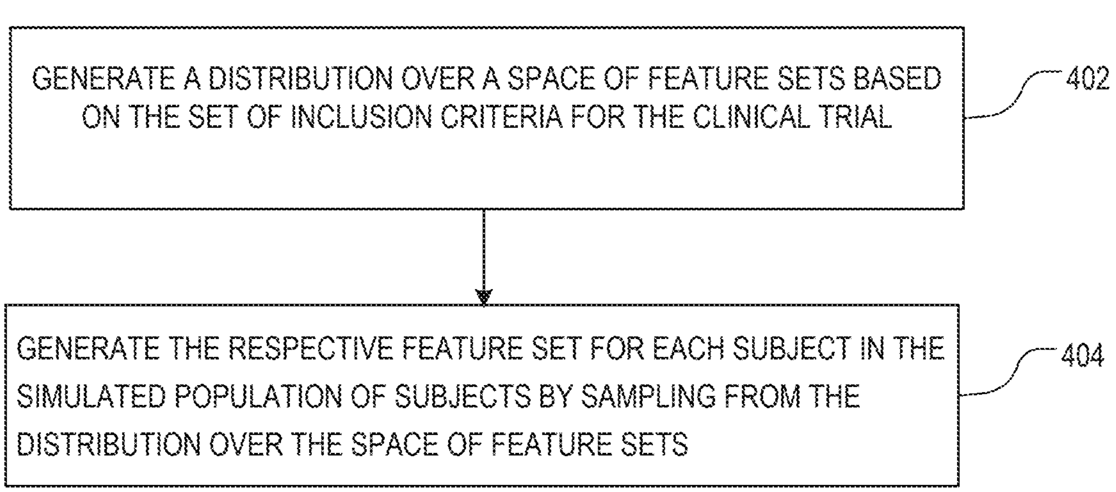
FIG. 4 is a flow diagram of an example process for obtaining data defining a simulated population of subjects satisfying the inclusion criteria for a clinical trial.

FIG. 4 is a flow diagram of an example process 400 for obtaining data defining a simulated population of subjects satisfying the inclusion criteria for a clinical trial. For convenience, the process 400 will be described as being performed by a system of one or more computers located in one or more locations. For example, a simulation system, e.g., the simulation system 100 of FIG. 1, appropriately programmed in accordance with this specification, can perform the process 400.

The system can first generate a distribution over a space of feature sets based on the set of inclusion criteria for the clinical trial (step 402).

The features in each feature set can include subject specific features, site level features, and trial level features. The subject specific features can include, for example, one or more demographic features of the subject (e.g., age of the subject, medical diagnoses of the subject), physiological features of the subject (e.g., features derived from analysis of tissue, blood, or urine samples from the subject), or a severity of a medical condition of the subject. The site-level features can include features characterizing a site at which the subject undergoes the clinical trial (e.g., a geographic location of the site or a facility type at the site). The trial level features can include, for example, a duration of the clinical trial (e.g., 60 days, 130 days, 200 days, etc.), a number of sites included in the clinical trial (e.g., 1 site, 3 sites, 10 sites, etc.), or a number of subjects included in the clinical trial (e.g., 20 subjects, 100, subjects, 1000 subjects, etc.).

The inclusion criteria can define features of the target population that are relevant to the research question of the clinical trial. The inclusion criteria can, for example, include type and stage of disease (e.g., early, late, etc.), previous treatment history (e.g., none, types of drugs used for treatment in the past, etc.), age range (e.g., 15-40, 70-80, 50-100, etc.), gender, etc.

The system can identify a real-world population of subjects that satisfy the set of inclusion criteria. The system can obtain a collection of feature sets that includes a respective feature set for each subject in the real-world population of subjects that satisfy the inclusion criteria. The system can generate the distribution over the space of feature sets by fitting the distribution over the space of feature sets to the collection of feature sets for the real-world population of subjects that satisfy the inclusion criteria. The system can extract the subset of real-world subjects that satisfy the set of inclusion criteria. In some examples, the system can then sample with replacement from the feature sets associated with these subjects. In other examples, the system can fit a parametric distribution function (e.g., a mixture of Gaussians) to the feature sets of these real-world subjects. The simulation system can then sample from that distribution in order to obtain the feature sets for the simulated subjects. The system can use any appropriate method of fitting a distribution function to a set of data by estimating the parameters of the distribution function e.g., maximum likelihood estimation, method of moments, Bayesian methods, least squares, etc.

The system can generate the respective feature set for each subject in a simulated population of subjects by sampling from the distribution over the space of feature sets (step 404). The simulated population of subjects can be used to simulate a clinical trial. Simulating a clinical trial using a simulated population of subjects is described in further detail above with reference to FIG. 2.

Figure 5:
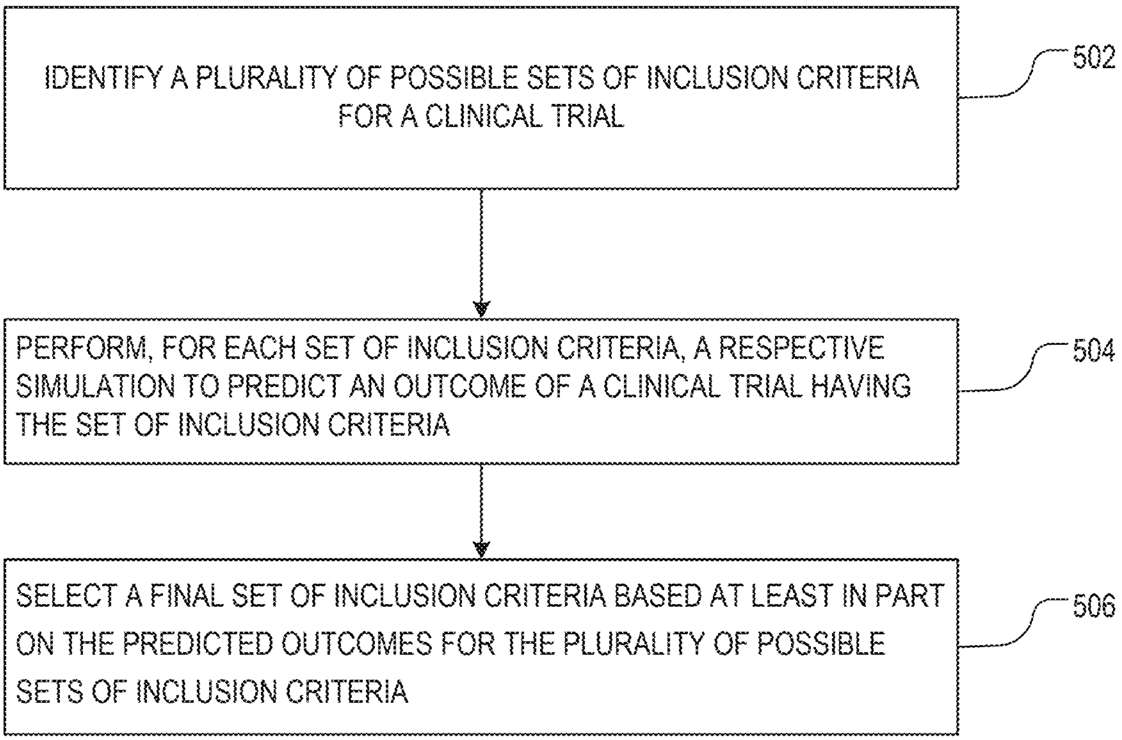
FIG. 5 is a flow diagram of an example process for performing an automated search through a space of possible inclusion criteria to optimize a predicted outcome of a clinical trial.

FIG. 5 is a flow diagram of an example process 500 for performing an automated search through a space of possible inclusion criteria to optimize a predicted outcome of a clinical trial. For convenience, the process 500 will be described as being performed by a system of one or more computers located in one or more locations. For example, a simulation system, e.g., the simulation system 100 of FIG. 1, appropriately programmed in accordance with this specification, can perform the process 500.

The system can identify a plurality of possible sets of inclusion criteria for the clinical trial (step 502). The inclusion criteria can define features of the target population that are relevant to the research question of the clinical trial. The inclusion criteria can, for example, include type and stage of disease (e.g., early, late, etc.), previous treatment history (e.g., none, types of drugs used for treatment in the past, etc.), age range (e.g., 15-40, 70-80, 50-100, etc.), gender, etc.

Each possible set of inclusion criteria can be unique. For example, the possible sets of inclusion criteria can include an age lower bound of 20, an age lower bound of 40, and an age lower bound of 60. Additionally, the possible sets of inclusion criteria can include a disease severity of high and a disease severity of low for each age lower bound.

The system can perform, for each set of inclusion criteria in the plurality of possible sets of inclusion criteria, a respective simulation to predict an outcome of a clinical trial having the set of inclusion criteria (step 504). Each predicted outcome can be a predicted measure of performance of a drug. The predicted outcome can be based on a measure of difference between a treatment group response and a control group response. The measure of difference can be, for example, a Cohen's D standardized mean difference. Each predicted outcome can be a distribution that has a measure of central tendency (e.g. a mean) and a measure of dispersions (e.g., a standard deviation).

The system can select a final set of inclusion criteria based at least in part on the predicted outcomes for the plurality of possible sets of inclusion criteria (step 506).

In some examples, the system may select a group of participants that is likely to respond favorably to a drug. The system can select a final set of inclusion criteria that reflects a group most likely to respond favorably to the drug. The system can select a final set of inclusion criteria that maximizes the mean (or the median, or another measure of central tendency) of the predicted outcome. In some examples, the system can additionally select a set of inclusion criteria based on: (i) a measure of central tendency of predicted outcomes associated with the inclusion criteria, and (ii) a measure of dispersion (e.g., variance) of predicted outcomes associated with the inclusion criteria. For instance, the system can select a set of inclusion criteria that maximize an objective function that includes a linear combination of: (i) a measure of central tendency of predicted outcome associated with the inclusion criteria (scaled by a positive coefficient), and (ii) a measure of dispersion of predicted outcomes associated with the inclusion criteria (scaled by a negative coefficient).

In another example, rather than identifying a set of inclusion criteria, the system can identify a set of exclusion criteria, e.g., such that a subject that satisfies the exclusion criteria is excluded from the clinical trial. For instance, the system can select a set of exclusion criteria that minimize a mean (or a median, or another measure of central tendency) of the predicted outcome. In some cases, the system can select a set of exclusion criteria based on: (i) a measure of central tendency of predicted outcomes associated with the exclusion criteria, and (ii) a measure of dispersion (e.g., variance) of predicted outcomes associated with the exclusion criteria. For instance, the system can select a set of exclusion criteria that minimize an objective function that includes a linear combination of: (i) a measure of central tendency of predicted outcome associated with the inclusion criteria (scaled by a positive coefficient), and (ii) a measure of dispersion of predicted outcomes associated with the inclusion criteria (scaled by a positive coefficient).

In some implementations the automated search through the space of possible inclusion criteria is performed in accordance with a black box optimization technique. A black box optimization (BBO) technique is an optimization technique where the structure of the objective function and the constraints defining the feasible region are unknown. BBOs can be used when the evaluation of the objective function and constraints involve a simulation and there are not explicit formulations that are easily exploited. The BBO can be used to select an optimal set of inclusion criteria. Examples of BBO techniques include the techniques described in Audet, Charles. *A survey on direct search methods for blackbox optimization and their applications*. Springer New York, 2014.

In some implementations, the system can perform the optimization over a sequence of iterations. At each iteration after the first iteration, the system can select one or more inclusion criteria to simulate at the iteration based on the outcomes associated with the inclusion criteria simulated at the previous iterations.

In some implementations, the automated search through the space of possible inclusion criteria is subject to one or more constraints. The constraints can include a constraint that, for a set of inclusion criteria to be feasible, at least a number or percentage of real-world subjects must be predicted to satisfy the inclusion criteria. This constraint can be imposed in order to ensure that the results of the simulated clinical trial can be replicated in a real-world clinical trial.

Figure 6A:
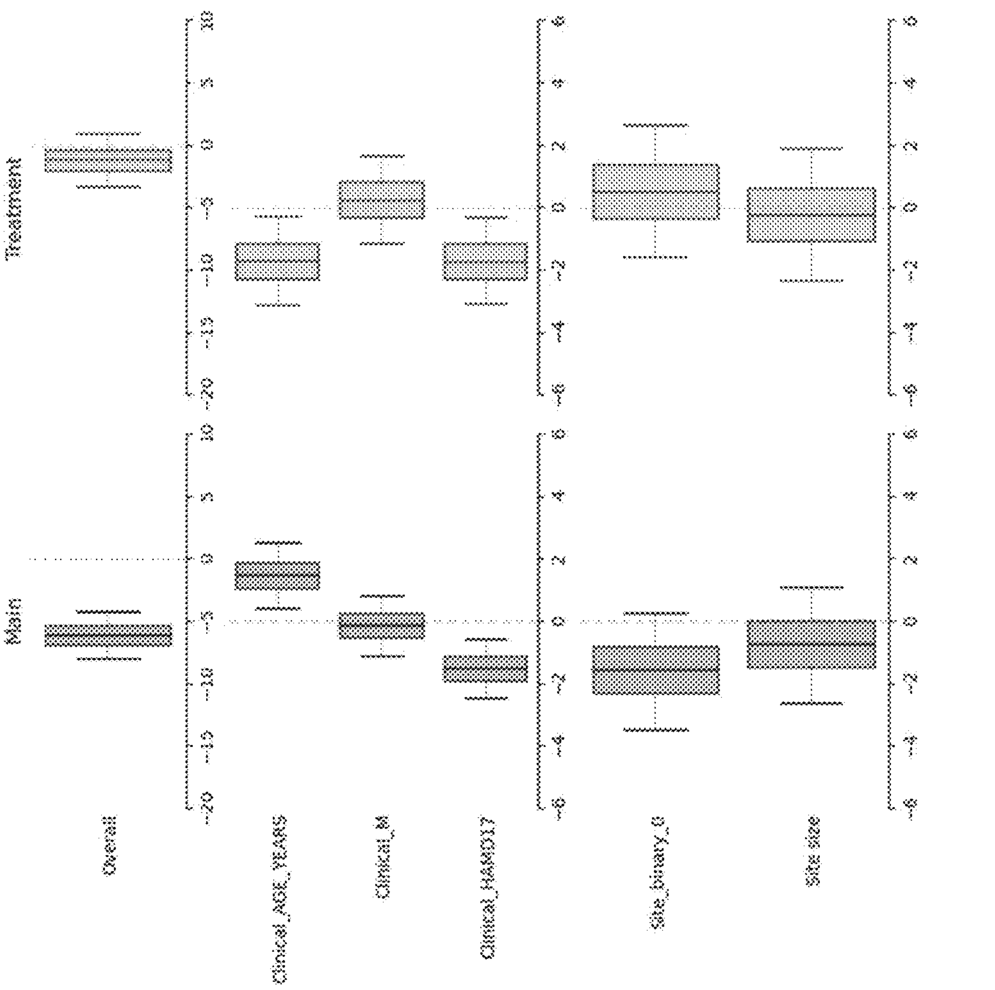
FIG. 6A illustrates an example of how the predicted responses of subjects are affected by each of the features processed by a machine learning model.

FIG. 6A illustrates an example of how the predicted responses of subjects are affected by each of the features processed by a machine learning model across the "main" (e.g., control) and "treatment" groups.

Figure 6B:
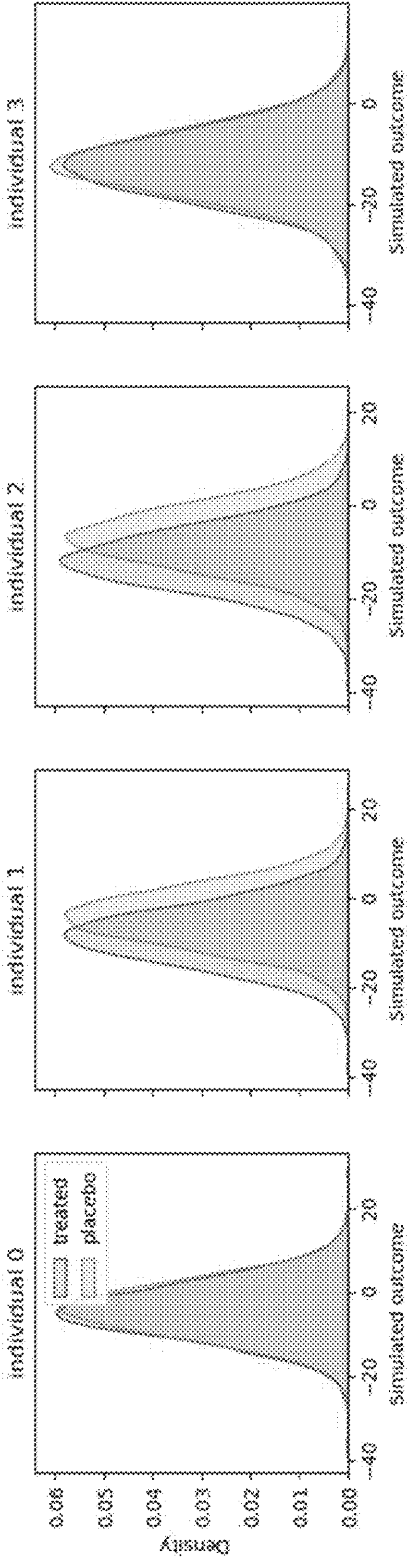
FIG. 6B illustrates an example of individual outcome distributions (as predicted by an ensemble of machine learning models) for 4 different subjects (trial participants).

FIG. 6B illustrates an example of individual outcome distributions (as predicted by an ensemble of machine learning models) for 4 different subjects (trial participants), each with their own characteristics, and how they are predicted to respond (e.g. in terms of change in a clinical severity score for depression) to a drug or a placebo.

Figure 6C:
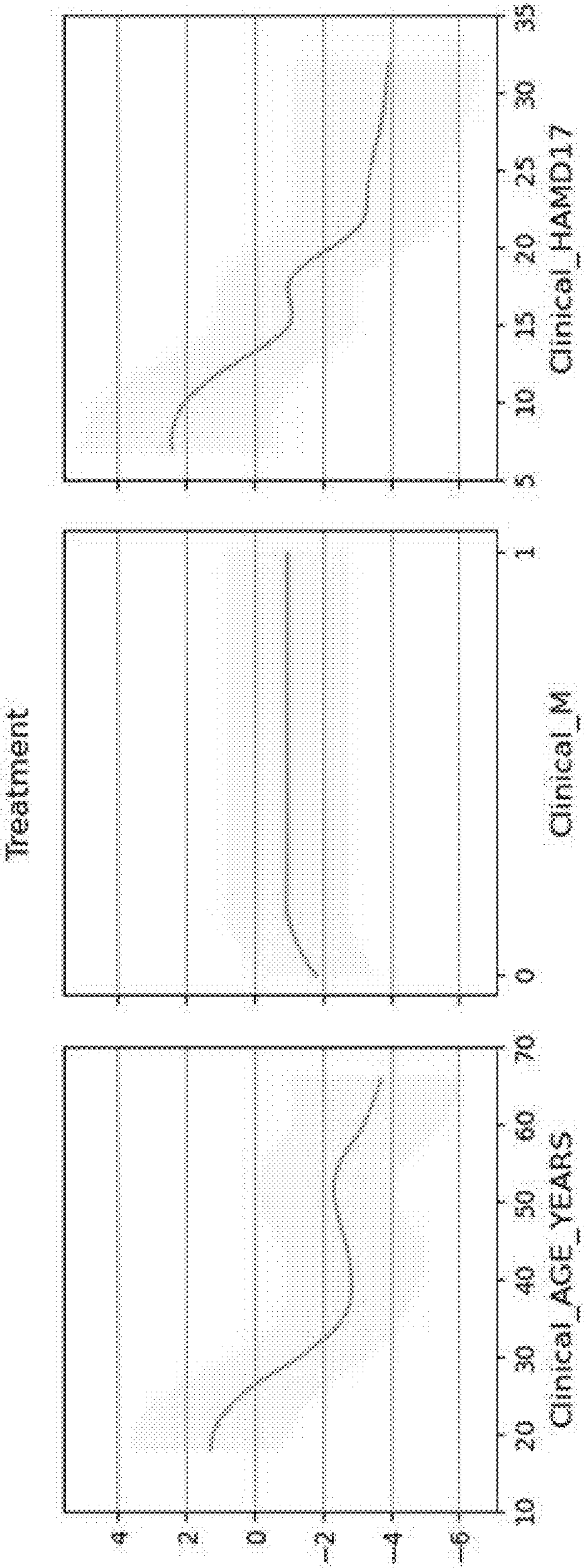
FIG. 6C illustrates an example of estimated non-linear relationships between several example covariates and the effect of treatment relative to placebo.

FIG. 6C illustrates an example of estimated non-linear relationships between several example covariates and the effect of treatment relative to placebo. The x-axis represents the covariate. On the y-axis, a lower score reflects more improvement on drug as compared to placebo.

Figure 7:
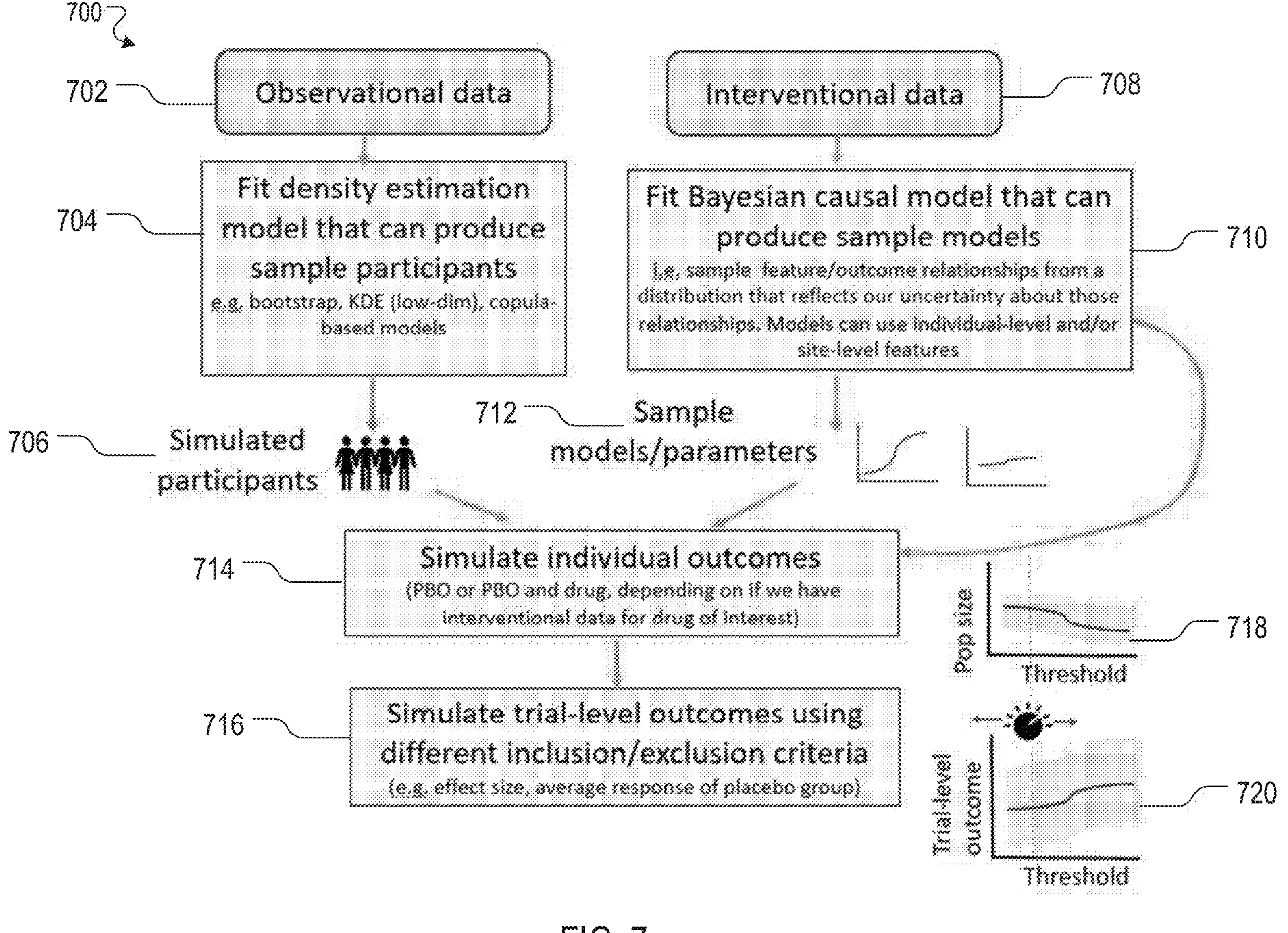
FIG. 7 shows an example of processing simulation data to generate a predicted outcome of a clinical trial.

FIG. 7 shows an example of processing simulation data to generate a predicted outcome of a clinical trial.

A simulation system can process observational data 702 using a density estimation model 704 to produce simulated subjects 706. The density estimation model can be, for example, a Bootstrap model, a kernel density estimation (KDE) model, a copula based model, etc. The observational data can include subject characteristics without an association with a subject outcome.

The simulation system can process interventional data 708 to fit a causal model 710 that can produce sample models 712 and model parameters. The simulation system can sample relationships between subject features and subject outcomes from a distribution that reflects uncertainty regarding these relationships. The interventional data can include any combination of individual level features, site level features, and trial level features.

The simulation system can use the simulated subjects and sample models to simulate outcomes for individual participants 714. Individual participants can be in either a treatment group or a control group.

The simulation system can simulate 716 trial-level outcomes 720 using various inclusion criteria 718 for the clinical trial and the outcomes for individual participants. Simulating trial-level outcomes is described below in further detail with reference to FIGS. 8 and 9.

Figure 8:
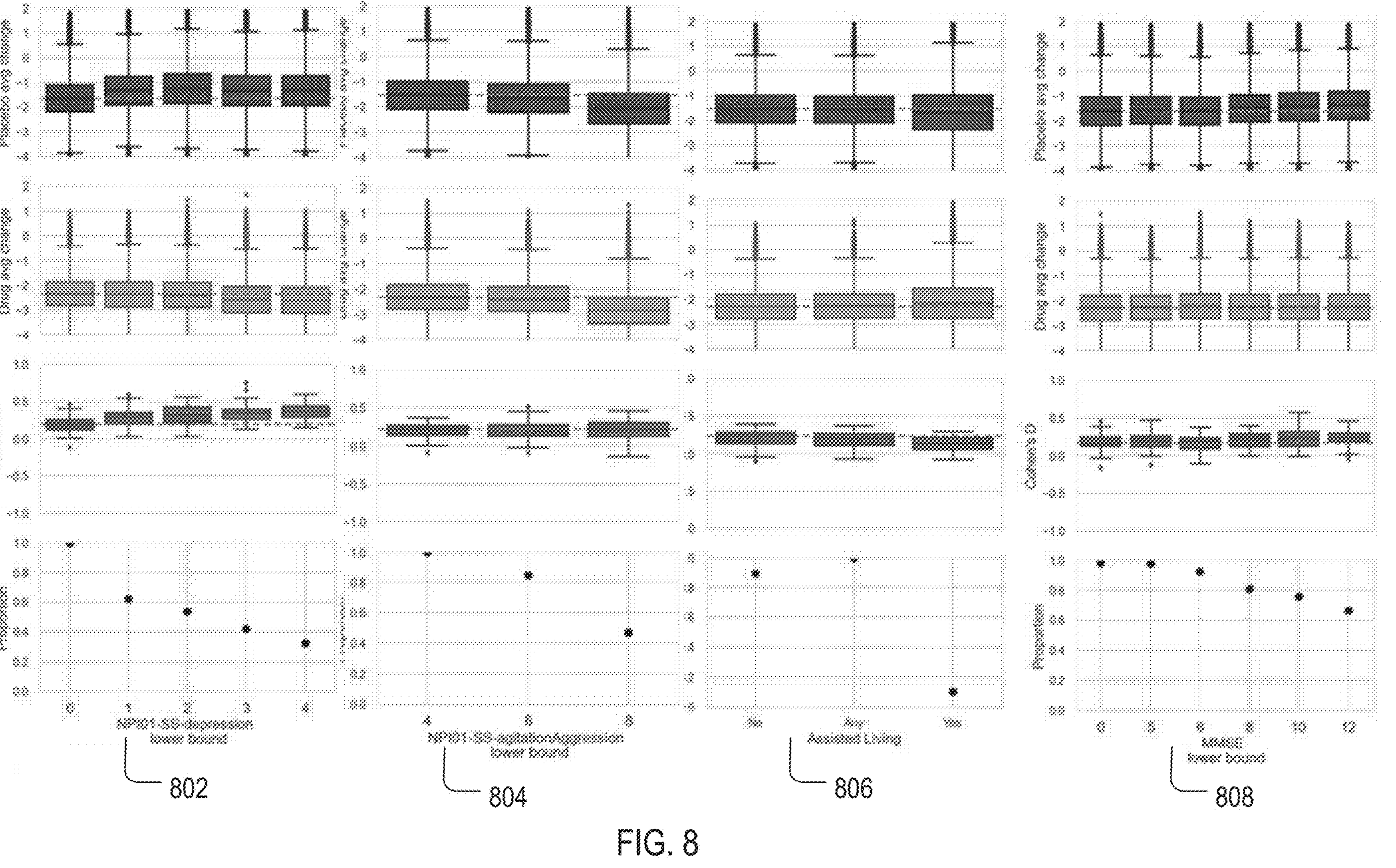
FIG. 8 shows examples of treatment group responses and control group responses for changes in inclusion criteria.

FIG. 8 shows examples of treatment group responses and control group responses for changes in inclusion criteria. The examples include treatment group responses and control group responses for changes in a depression lower bound 802, an aggression lower bound 804, an assisted living status 806, and a Mini-Mental State Examination (MMSE) score lower bound 808.

The example associated with changes in the depression lower bound 802 shows simulation results predicting the treatment group response, control group response, and effect size for subjects that have a NPI01-SS-depression score above various thresholds. For each threshold, the example 802 shows a distribution for the average change in a response score among subjects in the control group, a distribution for the average change in the response score among subjects the treatment group, and a distribution of effect size (i.e., the magnitude of the difference between the treatment group response and the control group response). Each distribution shows an average response score or effect size as well as a standard deviation. For example, when the threshold is a score of 4, the average effect size is a Cohen D's difference of 0.4. When the threshold is a score of 0 (i.e., all subjects are represented), the average effect size is a Cohen D's difference of 0.2.

Similarly, the example 804 shows simulation results predicting the treatment group response, control group response, and effect size for subjects that have a NPI01-SS-aggression score above various thresholds. The example 806 shows simulation results predicting the treatment group response, control group response, and effect size for subjects that live in an assisted living facility, subjects that don't live in an assisted living facility, and all subjects. The example 808 shows simulation results predicting the treatment group response, control group response, and effect size for subjects that have MMSE scores above various thresholds.

Clinical researchers can use these simulation results to select a condition that results in a target effect size with a desired probability.

Figure 9:
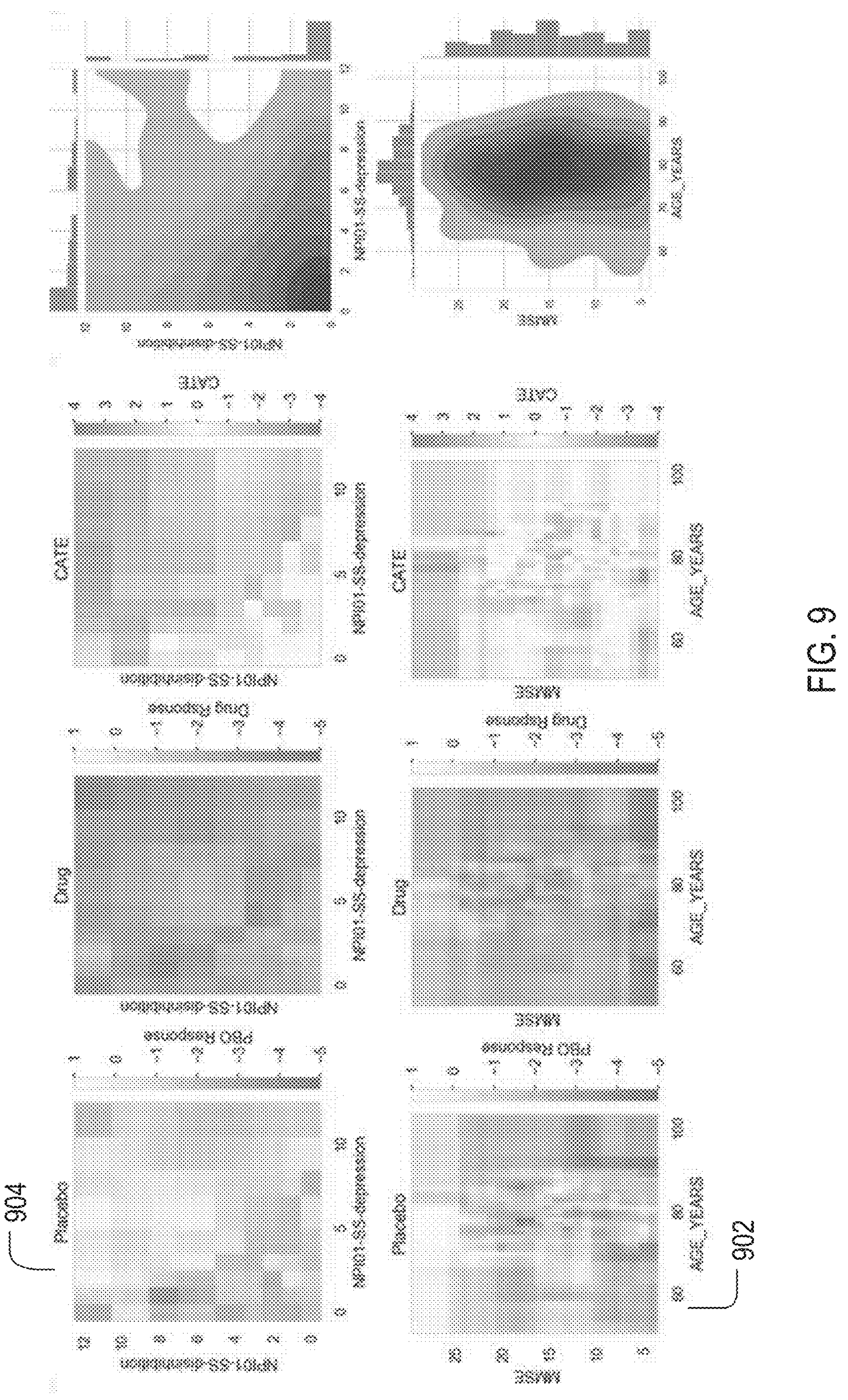
FIG. 9 shows examples of simulation results of adjusting two inclusion criteria simultaneously.

FIG. 9 shows examples of simulation results of adjusting two inclusion criteria simultaneously. The examples include control group responses, treatment group responses, and effect sizes for changes in subject characteristics.

The example 902 shows simulation results for combinations of various thresholds of subject age lower bounds and subject Mini-Mental State Examination (MMSE) score lower bounds. The example 902 shows a distribution for the average change in a response score among subjects in the control group, a distribution for the average change in the response score among subjects the treatment group, and a distribution of effect size (i.e., the magnitude of the difference between the treatment group response and the control group response).

The example 904 shows simulation results for combinations of various thresholds of subject NPI01-SS-disinhibition lower bounds and subject NPI01-SS-depression lower bounds. The example 904 shows a distribution for the average change in a response score among subjects in the control group, a distribution for the average change in the response score among subjects the treatment group, and a distribution of effect size (i.e., the magnitude of the difference between the treatment group response and the control group response).

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, or a Jax framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination.

Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by one or more computers for performing a computationally efficient simulation of a clinical trial using an ensemble of machine learning models and without requiring separate training of each machine learning model in the ensemble, the method comprising:

training, by the one or more computers, a probabilistic machine learning model to process an input feature set characterizing a subject to generate a predicted response score for the subject, wherein:

the predicted response score for the subject characterizes a predicted change in a medical condition of the subject during the clinical trial resulting from receiving a treatment; and each model parameter in a set of model parameters of the probabilistic machine learning model is associated with a respective distribution over possible values of the model parameter; and generating, by the one or more computers, the ensemble of machine learning models without requiring separate training of each machine learning model in the ensemble using the probabilistic machine learning model, comprising, for each machine learning model in the ensemble of machine learning models:

generating, by the one or more computers, the machine learning model as an instance of the probabilistic machine learning model by, for each model parameter of the probabilistic machine learning model, sampling a respective single value for the model parameter from the distribution over possible values of the model parameter;

performing, by the one or more computers, the simulation to predict an outcome of the clinical trial according to a set of inclusion criteria, comprising:

obtaining, by the one or more computers, data defining a simulated population of subjects satisfying the inclusion criteria for the clinical trial, wherein each subject in the simulated population of subjects is associated with a feature set characterizing the subject;

generating, by the one or more computers and using the ensemble of machine learning models, for each subject in the simulated population of subjects, a plurality of predicted response scores for the subject, wherein for each subject, generating the plurality of predicted response scores for the subject comprises:

processing, by the one or more computers and using each machine learning model in the ensemble of machine learning models, the feature set characterizing the subject in accordance with values of a set of model parameters of the machine learning model to generate a respective predicted response score for the subject; and determining, by the one or more computers, the predicted outcome of the clinical trial based on the plurality of predicted response scores for each subject in the simulated population of subjects; and determining, by the one or more computers, a final set of inclusion criteria for the clinical trial based at least in part on the simulation of the clinical trial.

2. The method of claim 1, wherein each machine learning model in the ensemble of machine learning models has: (i) a same model architecture, and (ii) a respective set of model parameters having values that are specific to the machine learning model.

3. The method of claim 1, wherein the probabilistic machine learning model comprises one or more of a neural network model; or a linear regression model; or a decision tree model.

4. The method of claim 1, wherein obtaining data defining the simulated population of subjects satisfying the inclusion criteria for the clinical trial comprises:

generating a distribution over a space of feature sets based on the set of inclusion criteria for the clinical trial; and generating the feature set for each subject in the simulated population of subjects by sampling from the distribution over the space of feature sets.

5. The method of claim 4, wherein generating the distribution over the space of feature sets based on the set of inclusion criteria for the clinical trial comprises:

identifying a real-world population of subjects that satisfy the set of inclusion criteria;

obtaining a collection of feature sets that includes a respective feature set for each subject in the real-world population of subjects that satisfy the inclusion criteria; and generating the distribution over the space of feature sets by fitting the distribution over the space of feature sets to the collection of feature sets for the real-world population of subjects that satisfy the inclusion criteria.

6. The method of claim 1, wherein the clinical trial is a clinical trial for a drug; and wherein the simulated population of subjects is a treatment group that receive the drug; and wherein each predicted response score characterizes a predicted change in the medical condition of the subject during the clinical trial as a result of receiving the drug.

7. The method of claim 6, wherein determining the predicted outcome of the clinical trial for the drug based on the plurality of predicted response scores for each subject in the simulated population of subjects comprises:

determining a measure of central tendency of the predicted response scores for the subjects in the simulated population of subjects; and determining a measure of dispersion of the predicted response scores for the subjects in the simulated population of subjects.

8. The method of claim 6, wherein the drug is a drug for treating depression; and wherein each predicted response score for each subject characterizes a predicted change in a measure of depression of the subject during the clinical trial.

9. The method of claim 6, wherein performing the simulation to predict the outcome of the clinical trial having the set of inclusion criteria further comprises:

obtaining data defining a second simulated population of subjects satisfying the inclusion criteria for the clinical trial, wherein the second simulated population of subjects is a control group that does not receive the drug; and generating, for each subject in the second simulated population of subjects, a plurality of predicted response scores for the subject;

wherein the predicted outcome of the clinical trial for the drug is based on both: (i) the plurality of predicted response scores for each subject in the simulated population of subjects that is the treatment group, and (ii) the plurality of predicted response scores for each subject in the second simulated population of subjects that is the control group.

10. The method of claim 9, wherein the predicted outcome of the clinical trial is based on a measure of difference between: (i) the plurality of predicted response scores for each subject in the simulated population of subjects that is the treatment group, and (ii) the plurality of predicted response scores for each subject in the second simulated population of subjects that is the control group.

11. The method of claim 1, wherein the clinical trial is for a drug, and further comprising:

selecting the set of inclusion criteria for the clinical trial based at least in part on the predicted outcome of the clinical trial having the inclusion criteria; and for each of one or more real-world subjects:

determining that the real-world subject satisfies the set of inclusion criteria for the clinical trial; and in response, determining that the real-world subject should receive the drug as part of the clinical trial.

12. The method of claim 11, further comprising, for each of the one or more real-world subjects:

administering the drug to the real-world subject in response to determining that the real-world subject should receive the drug as part of the clinical trial.

13. The method of claim 1, further comprising performing an automated search through a space of possible inclusion criteria to optimize a predicted outcome of the clinical trial.

14. The method of claim 13, wherein performing the automated search through the space of possible inclusion criteria to optimize the predicted outcome of the clinical trial comprises:

identifying a plurality of possible sets of inclusion criteria for the clinical trial;

performing, for each set of inclusion criteria in the plurality of possible sets of inclusion criteria, a respective simulation to predict an outcome of a clinical trial having the set of inclusion criteria; and selecting a final set of inclusion criteria based at least in part on the predicted outcomes for the plurality of possible sets of inclusion criteria.

15. The method of claim 13, wherein the automated search through the space of possible inclusion criteria is performed in accordance with a black box optimization technique.

16. The method of claim 13, wherein the automated search through the space of possible inclusion criteria is subject to one or more constraints;

wherein the one or more constraints include a constraint that, for a set of inclusion criteria to be feasible, at least a number or percentage of real-world subjects are predicted to satisfy the inclusion criteria.

17. A system comprising:

one or more computers; and one or more storage devices communicatively coupled to the one or more computers, wherein the one or more storage devices store instructions that, when executed by the one or more computers, cause the one or more computers to perform operations for performing a computationally efficient simulation of a clinical trial using an ensemble of machine learning models and without requiring separate training of each machine learning model in the ensemble, the operations comprising:

training a probabilistic machine learning model to process an input feature set characterizing a subject to generate a predicted response score for the subject, wherein:

the predicted response score for the subject characterizes a predicted change in a medical condition of the subject during the clinical trial resulting from receiving a treatment; and each model parameter in a set of model parameters of the probabilistic machine learning model is associated with a respective distribution over possible values of the model parameter; and generating the ensemble of machine learning models without requiring separate training of each machine learning model in the ensemble using the probabilistic machine learning model, comprising, for each machine learning model in the ensemble of machine learning models:

generating the machine learning model as an instance of the probabilistic machine learning model by, for each model parameter of the probabilistic machine learning model, sampling a respective single value for the model parameter from the distribution over possible values of the model parameter;

performing the simulation to predict an outcome of the clinical trial according to a set of inclusion criteria, comprising:

obtaining data defining a simulated population of subjects satisfying the inclusion criteria for the clinical trial, wherein each subject in the simulated population of subjects is associated with a feature set characterizing the subject;

generating, using the ensemble of machine learning models and for each subject in the simulated population of subjects, a plurality of predicted response scores for the subject, wherein for each subject, generating the plurality of predicted response scores for the subject comprises:

processing, by each machine learning model in the ensemble of machine learning models, the feature set characterizing the subject in accordance with values of a set of model parameters of the machine learning model to generate a respective predicted response score for the subject; and determining the predicted outcome of the clinical trial based on the plurality of predicted response scores for each subject in the simulated population of subjects; and determining a final set of inclusion criteria for the clinical trial based at least in part on the simulation of the clinical trial.

18. One or more non-transitory computer storage media storing instructions that when executed by one or more computers cause the one or more computers to perform operations for performing a computationally efficient simulation of a clinical trial using an ensemble of machine learning models and without requiring separate training of each machine learning model in the ensemble, the operations comprising:

training a probabilistic machine learning model to process an input feature set characterizing a subject to generate a predicted response score for the subject, wherein:

the predicted response score for the subject characterizes a predicted change in a medical condition of the subject during the clinical trial resulting from receiving a treatment; and each model parameter in a set of model parameters of the probabilistic machine learning model is associated with a respective distribution over possible values of the model parameter; and generating the ensemble of machine learning models without requiring separate training of each machine learning model in the ensemble using the probabilistic machine learning model, comprising, for each machine learning model in the ensemble of machine learning models:

generating the machine learning model as an instance of the probabilistic machine learning model by, for each model parameter of the probabilistic machine learning model, sampling a respective single value for the model parameter from the distribution over possible values of the model parameter;

performing the simulation to predict an outcome of the clinical trial according to a set of inclusion criteria, comprising:

obtaining data defining a simulated population of subjects satisfying the inclusion criteria for the clinical trial, wherein each subject in the simulated population of subjects is associated with a feature set characterizing the subject;

generating, using the ensemble of machine learning models and for each subject in the simulated population of subjects, a plurality of predicted response scores for the subject, wherein for each subject, generating the plurality of predicted response scores for the subject comprises:

processing, by each machine learning model in the ensemble of machine learning models, the feature set characterizing the subject in accordance with values of a set of model parameters of the machine learning model to generate a respective predicted response score for the subject; and determining the predicted outcome of the clinical trial based on the plurality of predicted response scores for each subject in the simulated population of subjects; and determining a final set of inclusion criteria for the clinical trial based at least in part on the simulation of the clinical trial.

19. The non-transitory computer storage media of claim 18, wherein each machine learning model in the ensemble of machine learning models has: (i) a same model architecture, and (ii) a respective set of model parameters having values that are specific to the machine learning model.

20. The non-transitory computer storage media of claim 18, wherein the probabilistic machine learning model comprises one or more of: a neural network model; or a linear regression model; or a decision tree model.

* * * * *